(12) United States Patent
Kishida et al.

(10) Patent No.: US 12,133,706 B2
(45) Date of Patent: Nov. 5, 2024

(54) SURGICAL ROBOT

(71) Applicant: KAWASAKI JUKOGYO KABUSHIKI KAISHA, Kobe (JP)

(72) Inventors: Yuji Kishida, Kobe (JP); Toshihiko Takagi, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 494 days.

(21) Appl. No.: 17/238,251

(22) Filed: Apr. 23, 2021

(65) Prior Publication Data

US 2021/0330406 A1 Oct. 28, 2021

(30) Foreign Application Priority Data

Apr. 28, 2020 (JP) ................. 2020-079003

(51) Int. Cl.
*A61B 34/37* (2016.01)
*A61B 34/00* (2016.01)

(52) U.S. Cl.
CPC .............. *A61B 34/37* (2016.02); *A61B 34/74* (2016.02); *A61B 2034/742* (2016.02)

(58) Field of Classification Search
None
See application file for complete search history.

(56) References Cited

U.S. PATENT DOCUMENTS

| | | | | |
|---|---|---|---|---|
| 11,510,684 B2* | 11/2022 | Blackwell | ............ | A61B 17/147 |
| 2012/0071895 A1* | 3/2012 | Stahler | .................. | A61B 34/35 606/130 |
| 2012/0191269 A1* | 7/2012 | Chen | .................... | G05D 1/0016 701/2 |
| 2014/0094825 A1 | 4/2014 | Flaherty et al. | | |
| 2015/0080907 A1* | 3/2015 | Herrell | ................. | A61B 1/0016 606/130 |
| 2015/0282828 A1 | 10/2015 | Kishi et al. | | |
| 2017/0079731 A1* | 3/2017 | Griffiths | ................. | A61B 34/37 |
| 2017/0095299 A1* | 4/2017 | Hendrick | ......... | A61B 17/00234 |
| 2018/0101166 A1* | 4/2018 | Aldridge | ................ | B25J 9/1671 |
| 2018/0271732 A1 | 9/2018 | Yano et al. | | |
| 2018/0348744 A1* | 12/2018 | Cortsen | ................ | G05B 19/423 |
| 2020/0121403 A1 | 4/2020 | Awano et al. | | |
| 2021/0007814 A1* | 1/2021 | Shuma | ................... | A61B 34/74 |
| 2021/0128260 A1* | 5/2021 | Gonenc | .............. | A61B 17/3423 |
| 2021/0315646 A1* | 10/2021 | Brik | ....................... | A61B 17/17 |

FOREIGN PATENT DOCUMENTS

| | | |
|---|---|---|
| JP | 2006-150105 A | 6/2006 |
| JP | 2016-501042 A | 1/2016 |
| JP | 2018-094446 A | 6/2018 |
| JP | 2018-158009 A | 10/2018 |
| JP | 6469304 B1 | 2/2019 |
| JP | 2019-162427 A | 9/2019 |
| WO | 2013-181507 A1 | 12/2013 |
| WO | 2018/225788 A1 | 12/2018 |

* cited by examiner

*Primary Examiner* — Jaime Figueroa
*Assistant Examiner* — Arslan Azhar
(74) *Attorney, Agent, or Firm* — METROLEX IP LAW GROUP, PLLC; Robert L. Scott, Esq

(57) ABSTRACT

A surgical robot includes an arm configured to allow a medical device to be attached thereto, and an operation unit supported by the arm. The operation unit includes a joystick configured to operate movement of the medical device by the arm.

22 Claims, 7 Drawing Sheets

SURGICAL ROBOT

CROSS-REFERENCE TO RELATED APPLICATION

The priority application number JP2020-079003, Surgical Robot, Apr. 28, 2020, Yuji Kishida and Toshihiko Takagi, upon which this patent application is based, is hereby incorporated by reference.

BACKGROUND OF THE INVENTION

Field of the Invention

The present disclosure relates to a surgical robot, and more particularly, it relates to a surgical robot including an operation unit to operate an arm.

Description of the Background Art

Conventionally, a surgical robot including an operation unit to operate an arm is known. Such a surgical robot is disclosed in Japanese Patent Laid-Open No. 2019-162427, for example.

Japanese Patent Laid-Open No. 2019-162427 discloses a robot system (surgical robot) including an articulated probe, a surgical instrument, and a controller (hereinafter referred to as an arm). The surgical instrument is provided at the tip end of the articulated probe. The arm is configured to operate (move) the articulated probe and the surgical instrument. The robot system further includes a joystick. When an operator operates the joystick, a signal for operating the surgical instrument is output to the arm. In addition, the displacement, speed, and acceleration of the surgical instrument are operated according to the displacement (a way to tilt) of the joystick. The joystick is arranged apart from the arm (the articulated probe and the surgical instrument). For example, the joystick is arranged on a console or a table on which a patient is placed.

However, in the robot system as disclosed in Japanese Patent Laid-Open No. 2019-162427, at the time of surgery, the joystick arranged apart from the arm is operated such that the surgical instrument is operated. On the other hand, in the preparation stage before surgery, the arm is moved to move the surgical instrument to the vicinity of the patient. In this case, in the robot system as disclosed in Japanese Patent Laid-Open No. 2019-162427, the joystick is arranged apart from the arm, and thus it may be difficult to move the arm through the joystick so as to move the surgical instrument to the vicinity of the patient.

SUMMARY OF THE INVENTION

The present disclosure is intended to solve the above problem. The present disclosure aims to provide a surgical robot including an arm that is easily operable through an operation unit.

In order to attain the aforementioned object, a surgical robot according to a first aspect of the present disclosure includes an arm configured to allow a medical device to be attached thereto, and an operation unit supported by the arm. The operation unit includes a joystick configured to operate movement of the medical device by the arm.

In the surgical robot according to the first aspect of the present disclosure, as described above, the operation unit is supported by the arm. Accordingly, an operator can operate the operation unit in the vicinity of the arm unlike a case in which the arm is operated through the operation unit arranged apart from the arm, and thus the arm can be easily operated through the operation unit.

A surgical robot according to a second aspect of the present disclosure includes a robot arm including a plurality of joints, the robot arm being configured to allow a medical device to be attached to a tip end thereof, and an operation unit supported by the robot arm. The operation unit includes a joystick configured to operate the robot arm to move the medical device, and the joystick is configured to be operable by a finger of an operator that grasps the operation unit.

In the surgical robot according to the second aspect of the present disclosure, as described above, the operation unit is supported by the robot arm. Accordingly, the operator can operate the operation unit in the vicinity of the robot arm unlike a case in which the robot arm is operated through the operation unit arranged apart from the robot arm, and thus the robot arm can be easily operated through the operation unit.

A surgical robot according to a third aspect of the present disclosure includes a robot arm including an arm portion including a plurality of joints, and a translation mechanism provided on a tip end of the arm portion, the translation mechanism being configured to allow a medical device to be attached thereto, the translation mechanism being configured to translate the medical device relative to the arm portion, and an operation unit supported by the robot arm. The operation unit includes a joystick configured to operate the arm portion to move the medical device, and a switch unit configured to be operable by a finger of an operator, the switch unit being configured to operate the arm portion and/or the translation mechanism to translate the medical device. The joystick and the switch unit are arranged apart from each other within a range operable by fingers of one hand of the operator in the operation unit.

In the surgical robot according to the third aspect of the present disclosure, as described above, the operation unit is supported by the robot arm. Accordingly, the operator can operate the operation unit in the vicinity of the robot arm unlike a case in which the robot arm is operated through the operation unit arranged apart from the robot arm, and thus the robot arm can be easily operated through the operation unit.

According to the present disclosure, as described above, the arm can be easily operated through the operation unit.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

Figure 1:
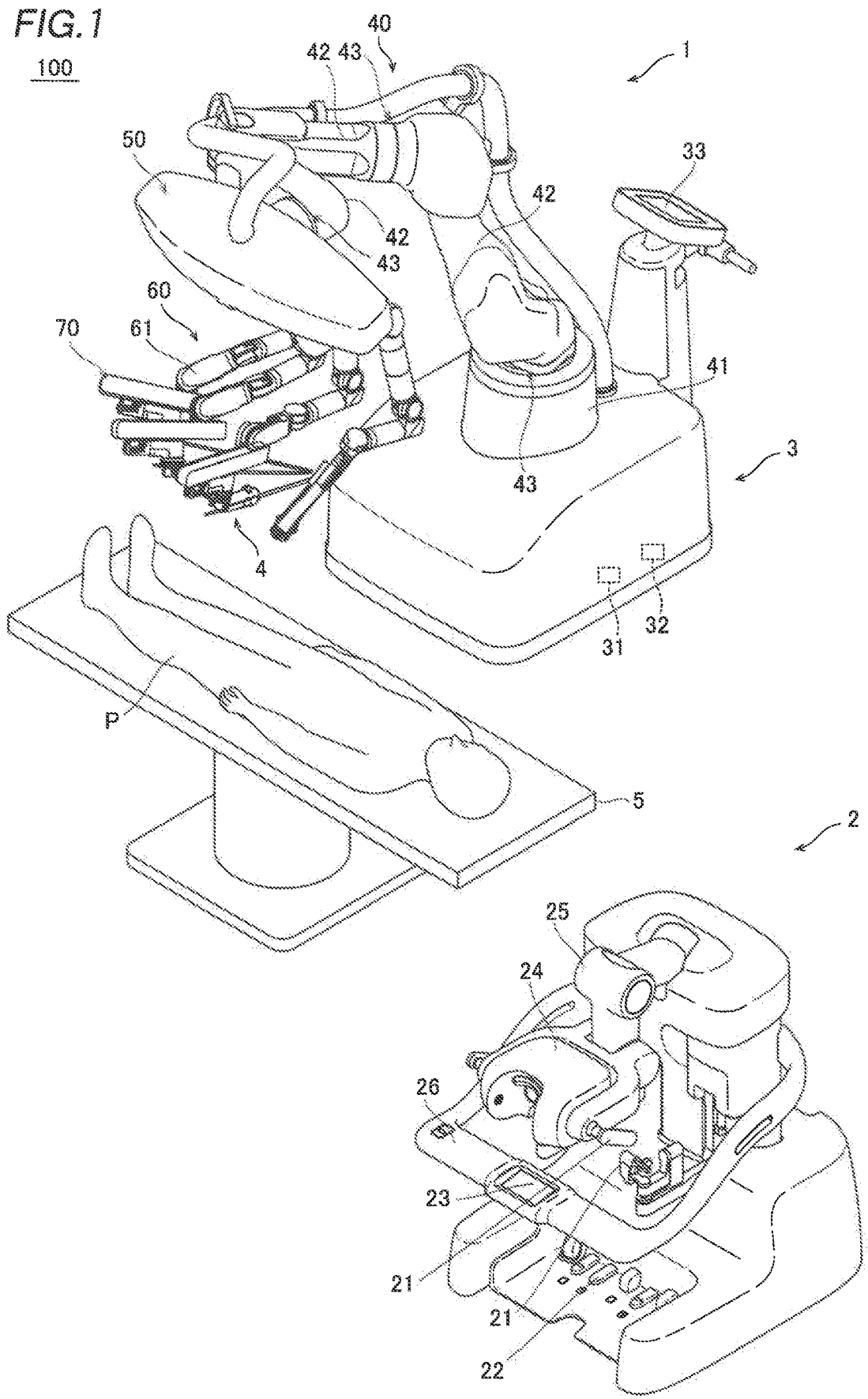
FIG. 1 is a diagram showing the configuration of a surgical system according to an embodiment of the present disclosure.

An embodiment of the present disclosure is hereinafter described with reference to the drawings.

The configuration of a surgical system 100 according to this embodiment is now described with reference to FIGS. 1 to 10. The surgical system 100 includes a medical manipulator 1 that is a patient P-side device and a remote operation device 2 that is an operator-side device configured to operate the medical manipulator 1. The medical manipulator 1 includes a medical cart 3 configured to support and transport the medical manipulator 1, and is configured to be movable. The remote operation device 2 is arranged apart from the medical manipulator 1, and the medical manipulator 1 is configured to be remotely operated by the remote operation device 2. A surgeon inputs a command to the remote operation device 2 to cause the medical manipulator 1 to perform a desired operation. The remote operation device 2 transmits the input command to the medical manipulator 1. The medical manipulator 1 operates based on the received command. The medical manipulator 1 is arranged in an operating room that is a sterilized sterile field. The medical manipulator 1 is an example of a "surgical robot" in the claims.

The remote operation device 2 is arranged inside or outside the operating room, for example. The remote operation device 2 includes operation manipulator arms 21, operation pedals 22, a touch panel 23, a monitor 24, a support arm 25, and a support bar 26. The operation manipulator arms 21 define operation handles for the surgeon to input commands. The monitor 24 is a scope-type display that displays an image captured by an endoscope. The support arm 25 supports the monitor 24 so as to align the height of the monitor 24 with the height of the surgeon's face. The touch panel 23 is arranged on the support bar 26. The surgeon's head is detected by a sensor (not shown) provided in the vicinity of the monitor 24 such that the medical manipulator 1 can be operated by the remote operation device 2. The surgeon operates the operation manipulator arms 21 and the operation pedals 22 while visually recognizing an affected area on the monitor 24. Thus, a command is input to the remote operation device 2. The command input to the remote operation device 2 is transmitted to the medical manipulator 1.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote operation device 2.

The medical cart 3 includes an input 33. The input 33 is configured to receive operations to move a positioner 40, an arm base 50, and a plurality of arms 60 or change their postures mainly in order to prepare for surgery before the surgery.

Figure 2:
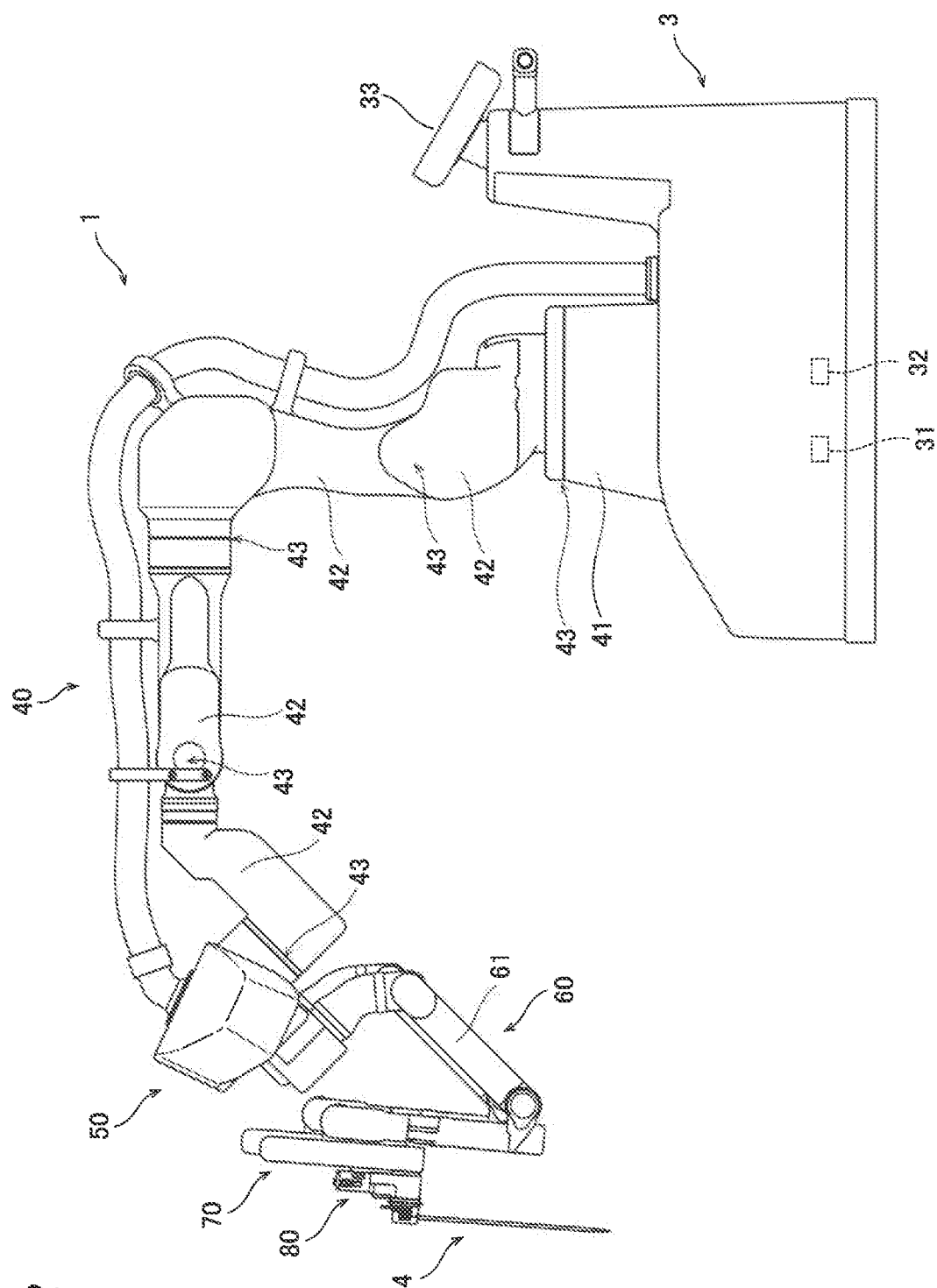
FIG. 2 is a diagram showing the configuration of a medical manipulator according to the embodiment of the present disclosure.

As shown in FIGS. 1 and 2, the medical manipulator 1 is arranged in the operating room. The medical manipulator 1 includes the medical cart 3, the positioner 40, the arm base 50, and the plurality of arms 60. The arm base 50 is attached to the tip end of the positioner 40. The arm base 50 has a relatively long rod shape (long shape). The bases of the plurality of arms 60 are attached to the arm base 50. Each of the plurality of arms 60 is configured to be able to take a folded posture (stored posture). The arm base 50 and the plurality of arms 60 are covered with sterile drapes (not shown) and used.

The positioner 40 includes a 7-axis articulated robot, for example. The positioner 40 is arranged on the medical cart 3. The positioner 40 is configured to move the position of the arm base 50 three-dimensionally.

The positioner 40 includes a base 41 and a plurality of links 42 coupled to the base 41. The plurality of links 42 are coupled to each other by joints 43.

As shown in FIG. 1, a medical device 4 is attached to the tip end of each of the plurality of arms 60. The medical device 4 includes a replaceable instrument or an endoscope assembly (not shown), for example.

Figure 3:
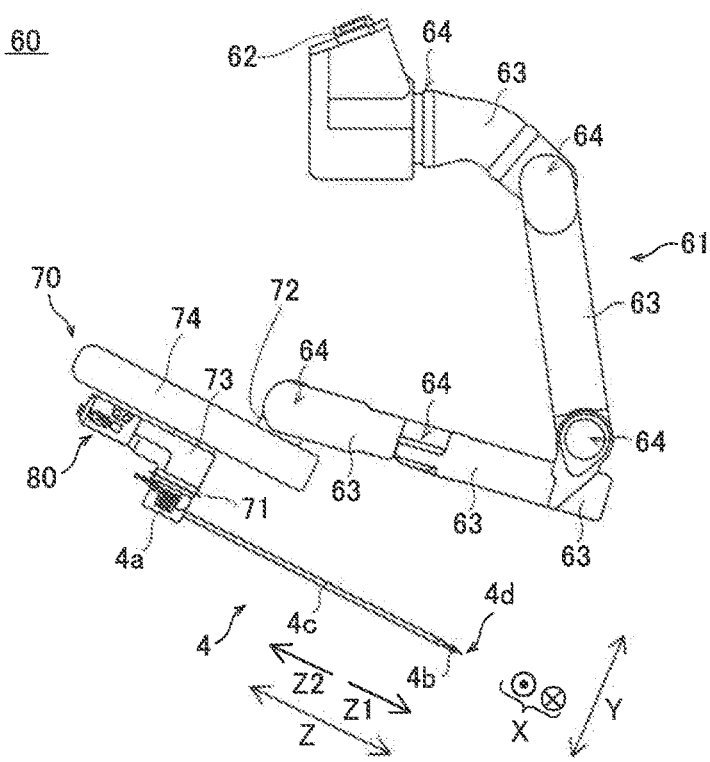
FIG. 3 is a diagram showing the configuration of an arm of the medical manipulator according to the embodiment of the present disclosure.

As shown in FIG. 3, the instrument as the medical device 4 includes a driven unit 4a driven by a servomotor M2 provided in a holder 71 of each of the arms 60. An end effector 4b is provided at the tip end 4d of the instrument. The end effector 4b includes a pair of forceps, a pair of scissors, a grasper, a needle holder, a microdissector, a stable applier, a tacker, a suction cleaning tool, a snare wire, a clip applier, etc. as instruments having joints. The end effector 4b includes a cutting blade, a cautery probe, a washer, a catheter, a suction orifice, etc. as instruments having no joint. The medical device 4 includes a shaft 4c that connects the driven unit 4a to the end effector 4b. The driven unit 4a, the shaft 4c, and the end effector 4b are arranged along a Z direction.

The configuration of the arms 60 is now described in detail.

As shown in FIG. 3, each of the arms 60 includes an arm portion 61 (a base 62, links 63, and joints 64) and a translation mechanism 70 provided at the tip end of the arm portion 61. The arms 60 are configured to three-dimensionally move the tip end sides with respect to the base sides (arm base 50) of the arms 60. The plurality of arms 60 have the same configuration as each other.

In this embodiment, the translation mechanism 70 is provided on the tip end side of the arm portion 61, and the medical device 4 is attached to the translation mechanism 70. The translation mechanism 70 translates the medical device 4 in a direction in which the medical device 4 is inserted into the patient P. Furthermore, the translation mechanism 70 is configured to translate the medical device 4 relative to the arm portion 61. Specifically, the translation mechanism 70 includes the holder 71 configured to hold the medical device 4. The servomotor M2 (see FIG. 9) is housed in the holder 71. The servomotor M2 is configured to rotate a rotating body provided in the driven unit 4a of the medical device 4. The rotating body of the driven unit 4a is rotated such that the end effector 4b is operated.

The arms 60 are configured to be removable from the arm base 50.

The arm portion 61 includes a 7-axis articulated robot arm. The arm portion 61 includes the base 62 configured to attach the arm portion 61 to the arm base 50, and a plurality of links 63 coupled to the base 62. The plurality of links 63 are coupled to each other by the joints 64.

The translation mechanism 70 is configured to translate the medical device 4 attached to the holder 71 along the Z direction (a direction in which the shaft 4c extends) by translating the holder 71 along the Z direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the Z direction. The tip end side link 73 is moved along the Z direction relative to the base end side link 72 such that the medical device 4 provided on the holder 71 is translated along the Z direction. The tip end of the arm portion 61 is connected to the base end side link 72 so as to rotate the base end side link 72 about a Y direction orthogonal to the Z direction.

Figure 4:
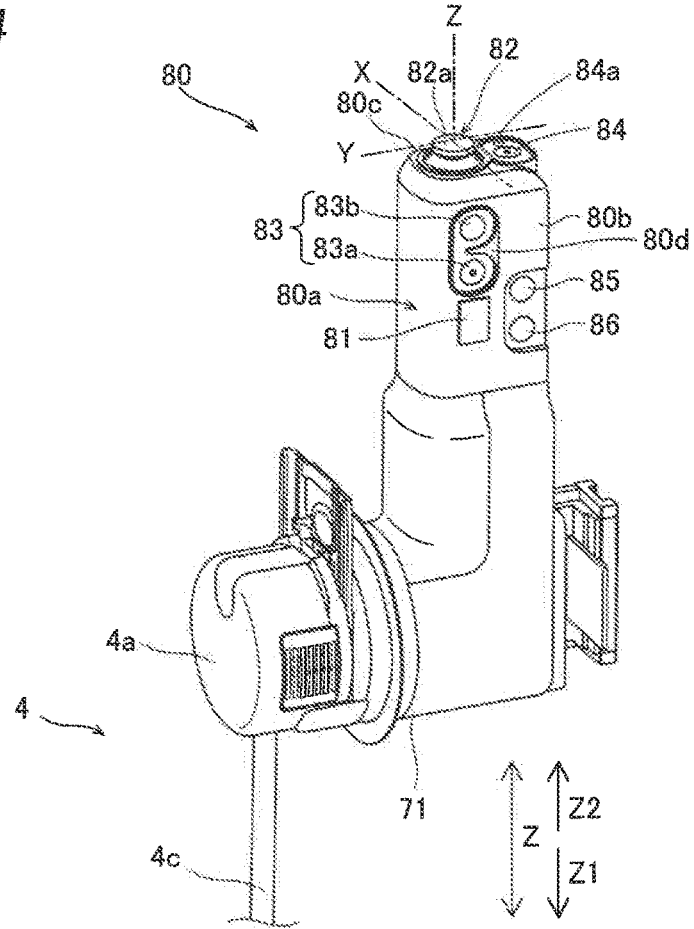
FIG. 4 is a perspective view showing the configuration of an operation unit of the medical manipulator according to the embodiment of the present disclosure.

In this embodiment, as shown in FIG. 4, the medical manipulator 1 includes an operation unit 80 supported by each of the arms 60 to operate the arm 60. The operation unit 80 includes enable switches 81, a joystick 82, and switch units 83. The enable switches 81 allow or disallow movement of the arm 60 through the joystick 82 and the switch units 83. The enable switches 81 get into a state of allowing movement of the medical device 4 by the arm 60 when an operator O (such as a nurse or a technician) grasps the operation unit 80 and presses the enable switches 81.

Specifically, the enable switches 81 are push-button switches to be pressed by the fingers of the operator O. The enable switches 81 are pressed such that it becomes possible to perform a control to energize servomotors M1 to M3 (perform a control to drive the servomotors M1 to M3). That is, it becomes possible to perform a control to move the arm 60 only while the enable switches 81 are pressed.

In this embodiment, the joystick 82 is configured to be operable by the finger of the operator O while the operator O grasps the operation unit 80. The operator O tilts the joystick 82 with their finger such that the joystick 82 is operated. The arm 60 is controlled to be moved according to a direction in which the joystick 82 is tilted and an angle at which the joystick 82 is tilted. The operator O brings their finger into contact with the tip end 82a of the joystick 82, moves their finger, and tilts the joystick 82 to operate the joystick 82. Only while the enable switches 81 are pressed, a signal input based on the operation of the joystick 82 is received. That is, when the enable switches 81 are not pressed, the arm 60 is not moved even when the joystick 82 is operated.

Figure 5:
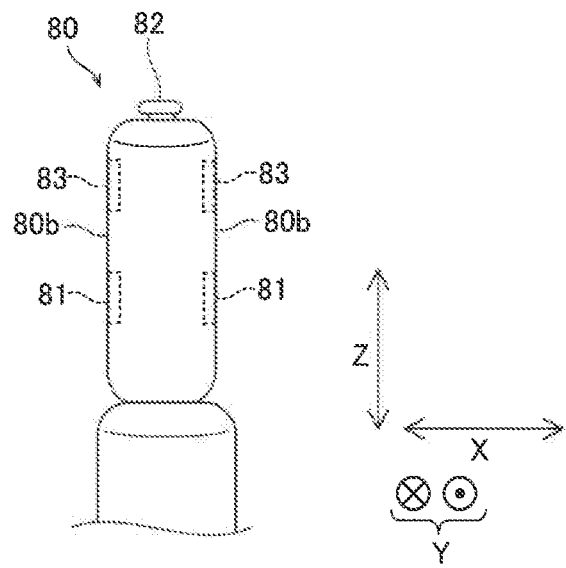
FIG. 5 is a side view showing the configuration of the operation unit of the medical manipulator according to the embodiment of the present disclosure.

The enable switches 81 are provided on the outer peripheral surface 80a of the operation unit 80, and allow movement of the medical device 4 by the arm 60 when the operator O grasps the outer peripheral surface 80a of the operation unit 80 and presses the enable switches 81. As shown in FIG. 5, a pair of enable switches 81 are provided on opposite sides of the outer peripheral surface 80a of the operation unit 80. In this embodiment, the enable switches 81 are provided on the opposite sides of the outer peripheral surface 80a of the operation unit 80 on which the switch units 83 are provided. Specifically, the cross-section of the operation unit 80 has a substantially rectangular shape, and each of the enable switches 81 and each of the switch units 83 are provided on each of surfaces 80b of the operation unit 80 that face each other. More specifically, the operation unit 80 has a substantially prismatic shape, and the enable switches 81 and the switch units 83 are provided on the side surfaces (the surfaces 80b along a longitudinal direction) of the substantially prismatic operation unit 80. The operator O grasps the outer peripheral surface 80a of the operation unit 80 and presses at least one of the enable switches 81 provided on the opposite sides of the outer peripheral surface 80a of the operation unit 80 to allow movement of the arm 60.

Thus, it is not necessary to press both of the enable switches 81 provided on the opposite sides of the outer peripheral surface 80a of the operation unit 80, and thus the burden on the operator O can be reduced while the convenience of the operator O is improved.

Figure 6:
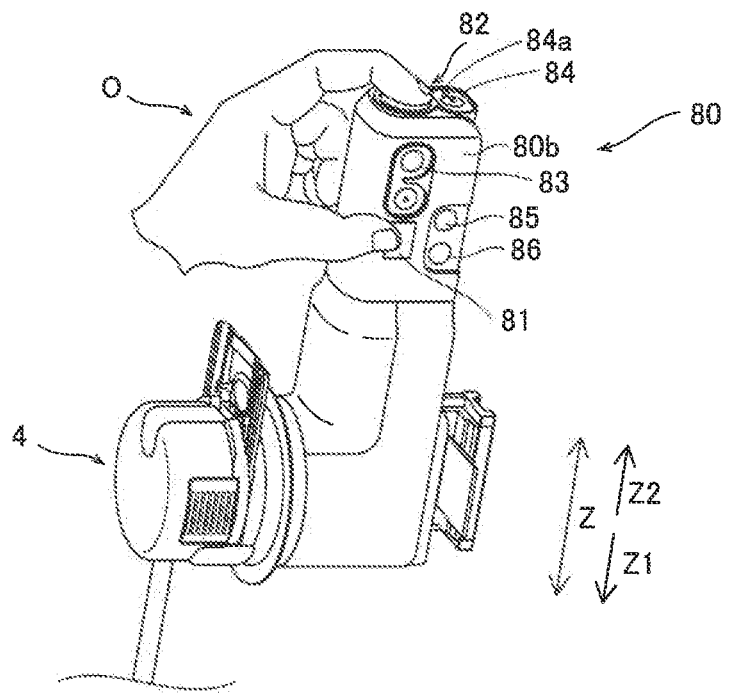
FIG. 6 is a diagram showing a state in which an operator grasps the operation unit of the medical manipulator according to the embodiment of the present disclosure.

As shown in FIG. 5, the joystick 82 is provided on an end face 80c of the operation unit 80 that intersects with the outer peripheral surface 80a. The joystick 82 is configured to be operable by the finger of the operator O while the operator O grasps the outer peripheral surface 80a of the operation unit 80 and presses the enable switches 81 to allow movement of the arm 60. For example, as shown in FIG. 6, the operator O operates the joystick 82 provided on the end face 80c of the operation unit 80 with their index finger or the like while pressing the pair of enable switches 81 provided on the outer peripheral surface 80a of the operation unit 80 with their thumb and middle finger or the like. Thus, substantially constant distances between the thumb and middle finger of the operator O that grasp the operation unit 80 and the index finger of the operator O that operates the joystick 82 can be easily maintained. Which fingers are used to operate the enable switches 81 and the joystick 82 is not limited to the above example.

In this embodiment, the joystick 82 is configured to operate movement of the medical device 4 by the arm 60 such that the tip end 4d (see FIG. 3) of the medical device 4 moves on a predetermined plane or the medical device 4 rotates about the tip end 4d of the medical device 4. The operation unit 80 includes the switch units 83 configured to operate movement of the medical device 4 by the arm 60 such that the tip end 4d of the medical device 4 moves along the longitudinal direction of the medical device 4. The predetermined plane on which the tip end 4d of the medical device 4 moves refers to a plane (an X-Y plane in FIG. 4) parallel to the end face 80c of the operation unit 80. The longitudinal direction of the medical device 4 refers to the Z direction orthogonal to the X-Y plane in FIG. 4. Coordinates represented by an X-axis, a Y-axis, and a Z-axis in FIG. 4 are referred to as a tool coordinate system (or a base coordinate system). When the switch units 83 are pressed while the enable switches 81 are pressed (while movement of the medical device 4 by the arm 60 is allowed), the tip end 4d of the medical device 4 is moved along the longitudinal direction of the medical device 4.

In this embodiment, the moving speed of the tip end 4d of the medical device 4 is changed according to the tilted state of the joystick 82, and when the joystick 82 is maximally tilted, the moving speed of the tip end 4d of the medical device 4 on the predetermined plane is maximized. The time until the switch units 83 are pressed by the operator O and the moving speed of the tip end 4d of the medical device 4 along the longitudinal direction of the medical device 4 is maximized is longer than the time until the joystick 82 is operated by the operator O and the moving speed of the tip end 4d of the medical device 4 is maximized. That is, the joystick 82 is operated such that the tip end 4d of the medical device 4 is moved at a relatively high speed. On the other hand, the switch units 83 are operated such that the tip end 4d of the medical device 4 is moved at a relatively low speed.

In this embodiment, each of the switch units 83 includes a switch 83a configured to move the tip end 4d of the medical device 4 in a direction in which the medical device 4 is inserted into the patient P, along the longitudinal direction of the medical device 4, and a switch 83b configured to move the tip end 4d of the medical device 4 in a direction opposite to the direction in which the medical device 4 is inserted into the patient P. Both the switch 83a and the switch 83b are push-button switches. Each of the switches 83a and 83b has a substantially circular shape. The switch 83a and the switch 83b are examples of a "first switch" and a "second switch" in the claims, respectively.

In this embodiment, the switch 83a is arranged on the side (Z1 direction side) on which the medical device 4 is inserted into the patient P on the operation unit 80. The switch 83b is arranged adjacent to the switch 83a on the side (Z2 direction side) opposite to the side on which the medical device 4 is inserted into the patient P on the operation unit 80. That is, the switch 83a and the switch 83b are arranged along the Z direction. Furthermore, the switch 83a and the switch 83b are arranged in a recess 80d provided so as to be recessed from the outer peripheral surface 80a of the operation portion 80.

In this embodiment, as shown in FIG. 5, the switch units 83 are provided on the opposite sides of the outer peripheral surface 80a of the operation portion 80. Specifically, the switch units 83 are provided on both side surfaces (the surfaces 80b along the longitudinal direction) of the operation portion 80 having a substantially prismatic shape, respectively. That is, a pair of switches 83a and a pair of switches 83b are provided on both side surfaces of the operation unit 80. The operator O grasps the outer peripheral surface 80a of the operation unit 80 and operates at least one of the switches 83a (switches 83b) provided on the opposite sides of the outer peripheral surface 80a of the operation unit 80 to cause the arm 61 and/or the translation mechanism 70 to translate the medical device 4.

In this embodiment, the switch units 83 increase the moving speed of the tip end 4d of the medical device 4 according to an increase in the length of time for which the operator O presses the switch units 83. That is, when the operator O continuously presses the switch units 83, the moving speed of the tip end 4d of the medical device 4 gradually increases. When the operator O releases pressing of the switch units 83, movement of the tip end 4d of the medical device 4 is stopped.

In this embodiment, the switch units 83 are operable by the fingers of the operator O, and the arm 61 and/or the translation mechanism 70 are operated through the switch units 83 to translate the medical device 4. The joystick 82 and the switch units 83 are arranged apart from each other within a range operable by the fingers of one hand of the operator O in the operation unit 80.

In this embodiment, when the switch units 83 are operated before a pivot position PP is set, the arm portion 61 is moved such that the tip end 4d of the medical device 4 is translated. When the switch units 83 are operated after the pivot position PP is set, the arm portion 61 is moved such that the tip end 4d of the medical device 4 is translated until the tip end 4d of the medical device 4 is moved by a predetermined distance from the pivot position PP. After the tip end 4d of the medical device 4 is moved by the predetermined distance from the pivot position PP, the translation mechanism 70 is moved such that the tip end 4d of the medical device 4 is translated. That is, after the tip end 4d of the medical device 4 is moved by the predetermined distance from the pivot position PP, the arm portion 61 is not moved but only the translation mechanism 70 is moved. The pivot position PP is described below.

Figure 8:
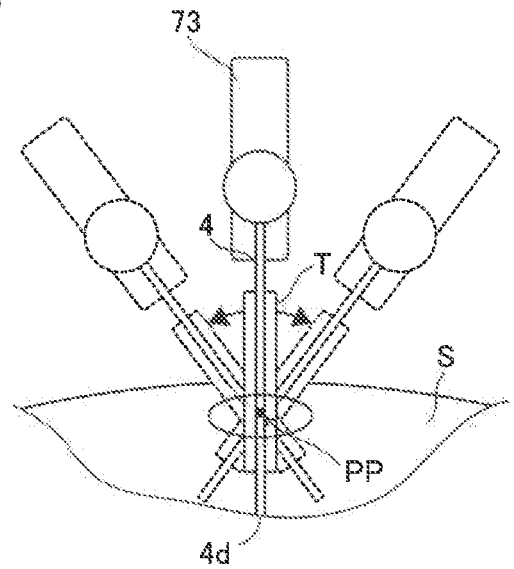
FIG. 8 is a diagram for illustrating rotation of the arm.

As shown in FIG. 4, pivot buttons 85 are provided adjacent to the enable switches 81 on the surfaces 80b of the operation unit 80. The pivot buttons 85 are configured to set the pivot position PP. As shown in FIG. 8, the pivot position PP refers to a fulcrum on which the medical device 4 attached to the arm 60 operates. Adjustment buttons 86 for optimizing the position of the arm 60 are provided on the surfaces 80b of the operation unit 80.

In this embodiment, as shown in FIG. 4, the operation unit 80 includes a mode switching button 84 configured to switch between a mode for translating the tip end 4d of the medical device 4 attached to the arm 60 in the predetermined plane (see FIG. 7) and a mode for rotating the medical device 4 about the tip end 4d of the medical device 4 (see FIG. 8). In the operation unit 80, the mode switching button 84 is arranged in the vicinity of the joystick 82. Specifically, on the end face 80c of the operation unit 80, the mode switching button 84 is provided adjacent to the joystick 82. The mode switching button 84 is a push-button switch. Furthermore, a mode indicator 84a is provided in the vicinity of the mode switching button 84. The mode indicator 84a is turned on or off such that a current mode (translation mode or rotation mode) is indicated. The mode switching button 84 is an example of a "mode switch" in the claims.

Figure 7:
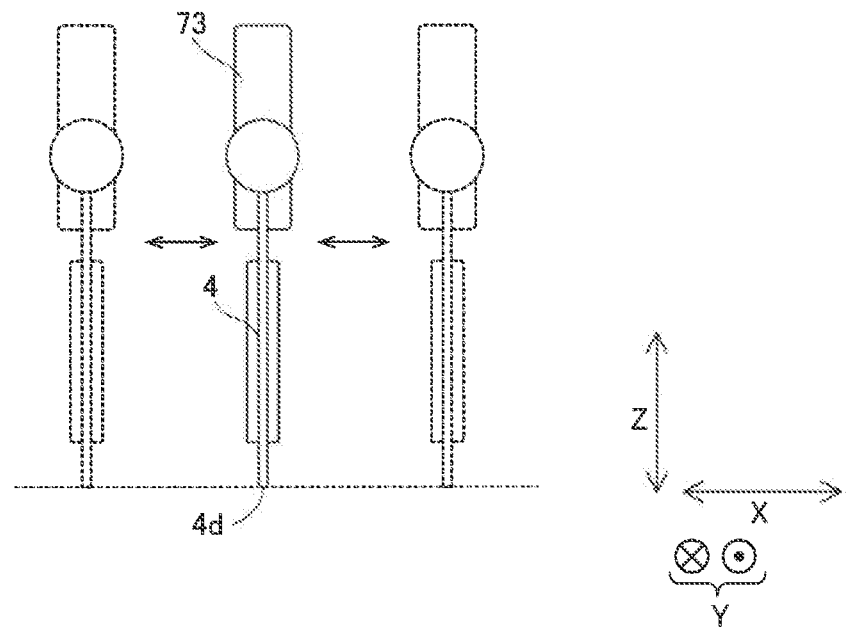
FIG. 7 is a diagram for illustrating translation of the arm.

As shown in FIG. 7, in the mode for translating the tip end 4d of the medical device 4, the arm 60 is moved through the joystick 82 such that the tip end 4d of the medical device 4 moves on the X-Y plane. As shown in FIG. 8, in the mode for rotating the medical device 4 about the tip end 4d of the medical device 4, when the pivot position PP is not taught, the arm 60 is moved through the joystick 82 such that the medical device 4 rotates about the tip end 4d of the end effector 4b, and when the pivot position PP is taught, the arm 60 is moved through the joystick 82 such that the medical device 4 rotates about the pivot position PP as a fulcrum. After the pivot position PP is set, the translation mode cannot be set. When the shaft 4c of the medical device 4 is inserted into a trocar T, the medical device 4 is rotated while the shaft 4c is restrained with the pivot position PP as a fulcrum.

In this embodiment, as shown in FIG. 3, the operation unit 80 is provided on the translation mechanism 70. The operation unit 80 is attached to the translation mechanism 70 so as to be adjacent to the medical device 4 attached to the translation mechanism 70. Specifically, the operation unit 80 is attached to the tip end side link 73 of the translation mechanism 70. The operation unit 80 is arranged adjacent to the driven unit 4a of the medical device 4.

Figure 9:
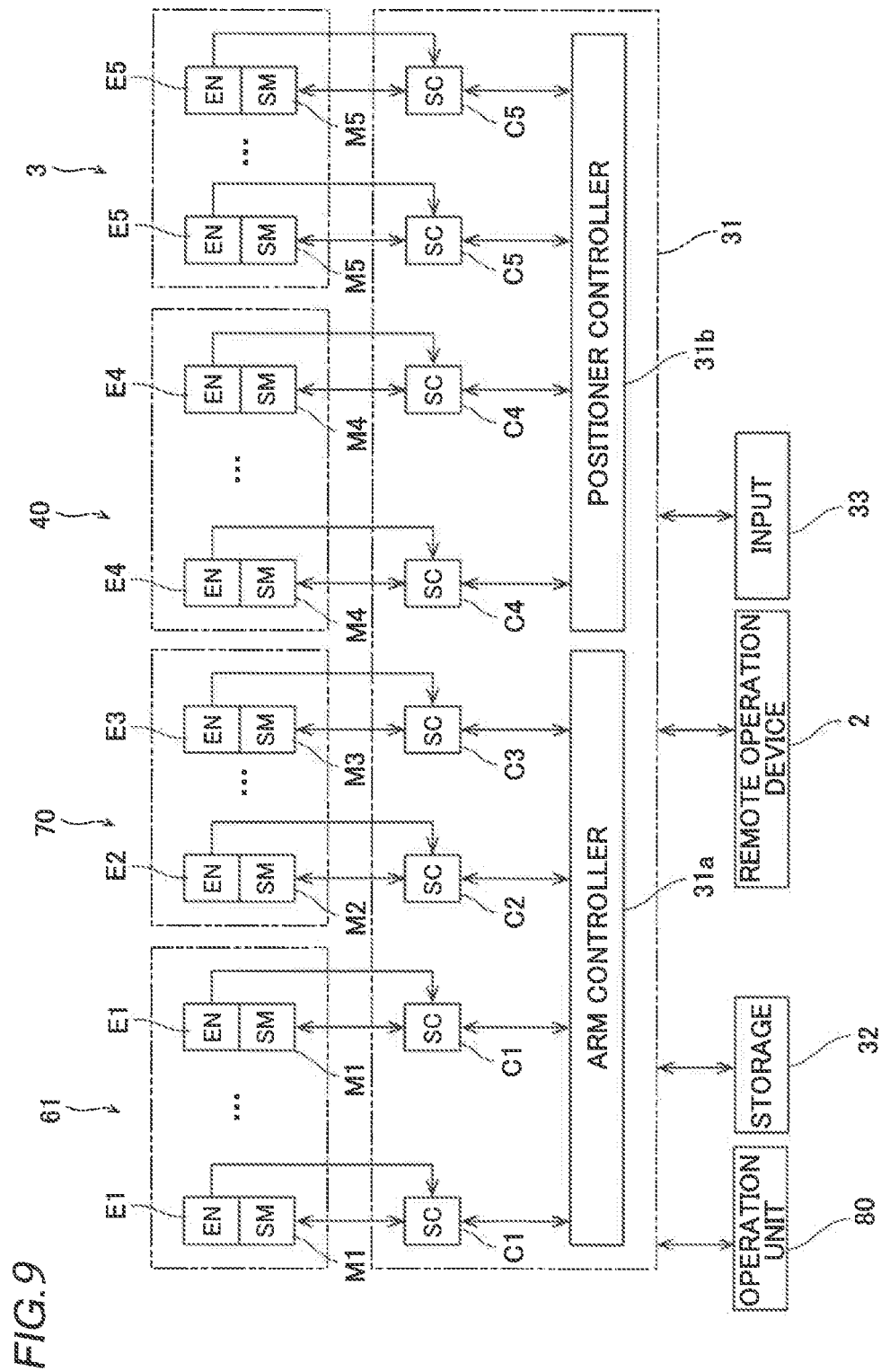
FIG. 9 is a block diagram showing the configuration of a controller of the medical manipulator according to the embodiment of the present disclosure.

As shown in FIG. 9, the arm 60 includes a plurality of servomotors M1, encoders E1, and speed reducers (not shown) so as to correspond to a plurality of joints 64 of the arm portion 61. The encoders E1 are configured to detect the rotation angles of the servomotors M1. The speed reducers are configured to slow down rotation of the servomotors M1 to increase the torques.

As shown in FIG. 9, the translation mechanism 70 includes the servomotor M2 configured to rotate the rotating body provided in the driven unit 4a of the medical device 4, the servomotor M3 configured to translate the medical device 4, encoders E2 and E3, and speed reducers (not shown). The encoders E2 and E3 are configured to detect the rotation angles of the servomotors M2 and M3, respectively. The speed reducers are configured to slow down rotation of the servomotors M2 and M3 to increase the torques.

The positioner 40 includes a plurality of servomotors M4, encoders E4, and speed reducers (not shown) so as to correspond to a plurality of joints 43 of the positioner 40. The encoders E4 are configured to detect the rotation angles of the servomotors M4. The speed reducers are configured to slow down rotation of the servomotors M4 to increase the torques.

The medical cart 3 includes servomotors M5 configured to drive a plurality of front wheels (not shown) of the medical cart 3, respectively, encoders E5, and speed reducers (not shown). The encoders E5 are configured to detect the rotation angles of the servomotors M5. The speed reducers are configured to slow down rotation of the servomotors M5 to increase the torques.

The controller 31 of the medical cart 3 includes an arm controller 31a that controls movement of the plurality of arms 60 based on commands, and a positioner controller 31b that controls movement of the positioner 40 and driving of the front wheels (not shown) of the medical cart 3 based on commands. Servo controllers C1 configured to control the servomotors M1 configured to drive the arm 60 are electrically connected to the arm controller 31a. The encoders E1 configured to detect the rotation angles of the servomotors M1 are electrically connected to the servo controllers C1.

A servo controller C2 configured to control the servomotor M2 configured to drive the medical device 4 is electrically connected to the arm controller 31a. The encoder E2 configured to detect the rotation angle of the servomotor M2 is electrically connected to the servo controller C2. A servo controller C3 configured to control the servomotor M3 configured to translate the translation mechanism 70 is electrically connected to the arm controller 31a. The encoder E3 configured to detect the rotation angle of the servomotor M3 is electrically connected to the servo controller C3.

An operation command input to the remote operation device 2 is input to the arm controller 31a. The arm controller 31a generates position commands based on the input operation command and the rotation angles detected by the encoders E1 (E2 or E3), and outputs the position commands to the servo controllers C1 (C2 or C3). The servo controllers C1 (C2 or C3) generate torque commands based on the position commands input from the arm controller 31a and the rotation angles detected by the encoders E1 (E2 or E3), and output the torque commands to the servomotors M1 (M2 or M3). Thus, the arm 60 is moved according to the operation command input to the remote operation device 2.

The controller 31 (arm controller 31a) is configured to operate the arm 60 based on an input signal from the joystick 82 of the operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate torque commands based on the position commands input from the arm controller 31a and the rotation angles detected by the encoders E1, and output the torque commands to the servomotors M1. Thus, the arm 60 is moved according to the operation command input to the joystick 82.

The controller 31 (arm controller 31a) is configured to operate the arm 60 based on an input signal from each of the switch units 83 of the operation unit 80. Specifically, the arm controller 31a generates a position command(s) based on the input signal (operation command) input from each of the switch units 83 and the rotation angle(s) detected by the encoders E1 or the encoder E3, and outputs the position command(s) to the servo controllers C1 or the servo controller C3. The servo controllers C1 or the servo controller C3 generates a torque command(s) based on the position command(s) input from the arm controller 31a and the rotation angle(s) detected by the encoders E1 or the encoder E3, and outputs the torque command(s) to the servomotors M1 or the servomotor M3. Thus, the arm 60 is moved according to the operation command input to each of the switch units 83.

The controller 31 (arm controller 31a) is configured to perform a control to reduce a change in the moving speed of the arm 60 by performing at least one of setting an upper limit for the input signal from the joystick 82 or smoothing the input signal from the joystick 82. Specifically, the controller 31 controls movement of the arm 60 using the upper limit as the input signal when the upper limit is set for the input signal from the joystick 82, and an input signal exceeding the upper limit is input. Furthermore, the controller 31 smooths the input signal from the joystick 82 by a low-pass filter (LPF), for example. In this embodiment, the controller 31 performs both of setting the upper limit for the input signal from the joystick 82 and smoothing the input signal from the joystick 82.

The controller 31 (arm controller 31a) controls movement of the arm 60 based on an equation of motion for control shown in the following mathematical formula.

$$m\ddot{x} + c\dot{x} = F + \beta \dot{F}$$

Figure 10:
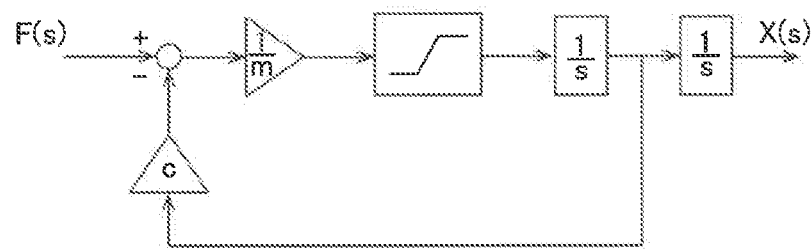
FIG. 10 is a diagram showing control blocks of the controller of the medical manipulator according to the embodiment of the present disclosure.

The controller 31 (arm controller 31a) controls movement of the arm 60 based on control blocks shown in FIG. 10. That is, the controller 31 (arm controller 31a) subtracts the product of the speed (a first order differential of x) and the viscosity coefficient c from the input signal F(s) from the joystick 82. Then, the subtracted value is multiplied by an inertia coefficient 1/m. When the multiplied value (=1/m(F(s)−c×speed)=acceleration=second order differential of x) exceeds the upper limit, the acceleration is set to the upper limit. Then, the acceleration is integrated to calculate the speed (the first order differential of x), and the speed is integrated to calculate a position X(s).

As shown in FIG. 9, servo controllers C4 configured to control the servomotors M4 that move the positioner 40 are electrically connected to the positioner controller 31b. The encoders E4 configured to detect the rotation angles of the servomotors M4 are electrically connected to the servo controllers C4. Servo controllers C5 configured to control the servomotors M5 that drive the front wheels (not shown) of the medical cart 3 are electrically connected to the positioner controller 31b. The encoders E5 configured to detect the rotation angles of the servomotors M5 are electrically connected to the servo controllers C5.

An operation command regarding preparation position setting, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate torque commands based on the position commands input from the positioner controller 31b and the rotation angles detected by the encoders E4, and output the torque commands to the servomotors M4. Thus, the positioner 40 is moved according to the operation command input to the input 33. Similarly, the positioner controller 31b moves the medical cart 3 based on an operation command from the input 33.

The procedure of surgery using the medical manipulator 1 is now described. In the surgery using the medical manipulator 1, the medical cart 3 is first moved to a predetermined position in the operating room by the operator O (such as a nurse or a technician). Next, the operator O operates a touch panel of the input 33 to operate the positioner 40 such that the arm base 50 and a surgical table 5 or the patient P have a desired positional relationship, and moves the arm base 50. Furthermore, the arm 60 is moved such that the trocar T (a working channel for inserting a surgical instrument or the like into the body cavity) arranged on the body surface of the patient P and the medical device 4 have a predetermined positional relationship. The joysticks 82 and the switch units 83 are operated by the operator O such that the plurality of arms 60 are moved to desired positions. Then, with the positioner 40 being stationary, the plurality of arms 60 and the medical devices 4 are operated based on commands from the remote operation device 2. Thus, the surgery with the medical manipulator 1 is performed.

Advantages of This Embodiment

According to this embodiment, the following advantages are achieved.

According to this embodiment, as described above, the operation unit 80 is supported by the arm 60. Accordingly, the operator O can operate the operation unit 80 in the vicinity of the arm 60 unlike a case in which the arm 60 is operated through the operation unit 80 arranged apart from the arm 60, and thus the arm 60 can be easily operated through the operation unit 80.

According to this embodiment, as described above, the joystick 82 is configured to operate movement of the medical device 4 by the arm 60 such that the tip end 4d of the medical device 4 moves on the predetermined plane, and the operation unit 80 includes the switch units 83 configured to operate movement of the medical device 4 by the arm 60 such that the tip end 4d of the medical device 4 moves along the longitudinal direction of the medical device 4. Accordingly, the operation of the medical device 4 on a plane by the arm 60 can be performed using the general joystick 82 configured to operate movement on the plane, and the tip end 4d of the medical device 4 can be moved along the longitudinal direction of the medical device 4 through the switch units 83. That is, the general joystick 82 and the switch units 83 are used together such that the tip end 4d of the medical device 4 can be moved three-dimensionally.

According to this embodiment, as described above, the joystick 82 is configured to maximize the moving speed of the tip end 4d of the medical device 4 on the predetermined plane when the joystick 82 is maximally tilted, and the time until the switch units 83 are pressed by the operator O and the moving speed of the tip end 4d of the medical device 4 along the longitudinal direction of the medical device 4 is maximized is longer than the time until the joystick 82 is operated by the operator O and the moving speed of the tip end 4d of the medical device 4 is maximized. Accordingly, the tip end 4d of the medical device 4 can be moved relatively gently through the switch units 83, and thus movement of the tip end 4d of the medical device 4 faster than the operator O intends can be significantly reduced or prevented.

According to this embodiment, as described above, each of the switch units 83 includes the switch 83a configured to move the tip end 4d of the medical device 4 in the direction in which the medical device 4 is inserted into the patient P, along the longitudinal direction of the medical device 4, and the switch 83b configured to move the tip end 4d of the medical device 4 in the direction opposite to the direction in which the medical device 4 is inserted into the patient P. Accordingly, the switch units 83 are individually provided for the direction in which the medical device 4 is moved, and thus movement of the medical device 4 in a direction unintended by the operator O due to erroneous operations on the switch units 83 can be significantly reduced or prevented.

According to this embodiment, as described above, the switch 83a is arranged on the side on which the medical device 4 is inserted into the patient P on the operation unit 80, and the switch 83b is arranged adjacent to the switch 83a on the side opposite to the side on which the medical device 4 is inserted into the patient P on the operation unit 80. Accordingly, the switch 83a and the switch 83b are arranged so as to correspond to the moving directions of the medical device 4, and thus erroneous operations on the switch units 83 can be further significantly reduced or prevented.

According to this embodiment, as described above, the switch units 83 increase the moving speed of the tip end 4d of the medical device 4 according to an increase in the length of time for which the operator O presses the switch units 83. Accordingly, the operation of the switch units 83 significantly reduces or prevents rapid movement of the tip end 4d of the medical device 4, and thus movement of the tip end 4d of the medical device 4 faster than the operator O intends can be further significantly reduced or prevented.

According to this embodiment, as described above, the switch units 83 are provided on the opposite sides of the outer peripheral surface 80a of the operation unit 80. Accordingly, unlike a case in which a switch unit 83 is provided on only one side of the outer peripheral surface 80a of the operation unit 80, the convenience of operation of the switch units 83 by the operator O can be improved.

According to this embodiment, as described above, the operation unit 80 further includes the enable switches 81 configured to allow or disallow movement of the arm 60, and the enable switches 81 are provided on the opposite sides of the outer peripheral surface 80a of the operation unit 80, respectively. Accordingly, the operator O grasps the operation unit 80 such that the operator O can press the enable switches 81 with their thumb, and can operate the joystick 82 or the switch units 83 with their index finger or middle finger, for example. That is, the operator O can operate movement of the medical device 4 by the arm 60 through the joystick 82 and the switch units 83 with their one hand.

According to this embodiment, as described above, the arm 60 includes the arm portion 61 including a 7-axis articulated robot and the translation mechanism 70 provided on the tip end 4d side of the arm portion 61, configured to allow the medical device 4 to be attached thereto, and configured to translate the medical device 4 in the direction in which the medical device 4 is inserted into the patient P, and until the pivot position PP, which serves as a fulcrum for movement of the arm 60, is set, the switch units 83 are operated such that the arm portion 61 is moved to translate the tip end 4d of the medical device 4. Accordingly, the medical device 4 is moved by the arm portion 61, and thus the tip end 4d of the medical device 4 can be moved to a desired position even when the translation mechanism 70 can translate the medical device 4 a relatively short distance.

According to this embodiment, after the pivot position PP is set, the switch units 83 are operated such that the arm portion 61 is moved to translate the tip end 4*d* of the medical device 4 until the tip end 4*d* of the medical device 4 moves a predetermined distance from the pivot position PP, and after the tip end 4*d* of the medical device 4 moves the predetermined distance from the pivot position PP, the translation mechanism 70 is moved to translate the tip end 4*d* of the medical device 4. Accordingly, after moving the predetermined distance from the pivot position PP, the medical device 4 can be accurately moved in a direction along the longitudinal direction of the medical device 4 by the translation mechanism 70.

According to this embodiment, as described above, the operation unit 80 further includes the mode switching button 84 configured to switch between the mode for translating the medical device 4 attached to the arm 60 and the mode for rotating the medical device 4 attached to the arm 60. Accordingly, the mode of movement of the medical device 4 attached to the arm 60 can be easily switched by simply switching the mode with the mode switching button 84.

According to this embodiment, as described above, on the operation unit 80, the mode switching button 84 is arranged in the vicinity of the joystick 82. Accordingly, the mode switching button 84 is arranged in the vicinity of the joystick 82, and thus an operation on the mode switching button 84 and an operation on the joystick 82 can be performed without changing the hand of the operator O with respect to the operation unit 80.

According to this embodiment, as described above, the arm 60 includes the arm portion 61 including a 7-axis articulated robot and the translation mechanism 70 provided on the tip end 4*d* side of the arm portion 61, configured to allow the medical device 4 to be attached thereto, and configured to translate the medical device 4 in the direction in which the medical device 4 is inserted into the patient P, and the operation unit 80 is attached to the translation mechanism 70. Accordingly, the operation unit 80 is arranged in the vicinity of the medical device 4, and thus an operation can be easily performed through the operation unit 80 to move the medical device 4 to a desired position by the arm 60.

According to this embodiment, as described above, the operation unit 80 is attached to the translation mechanism 70 so as to be adjacent to the medical device 4. Accordingly, the operation unit 80 is reliably arranged in the vicinity of the medical device 4, and thus an operation can be more easily performed through the operation unit 80 to move the arm 60 so as to move the medical device 4 to a desired position.

Modified Examples

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while one of the pair of enable switches 81 provided on the opposite sides of the outer peripheral surface 80*a* of the operation unit 80 is pressed to allow movement of the arm 60 in the aforementioned embodiment, the present disclosure is not limited to this. For example, both of the pair of enable switches 81 provided on the opposite sides of the outer peripheral surface 80*a* of the operation unit 80 may alternatively be pressed to allow movement of the arm 60.

While the pair of switch units 83 and the pair of enable switches 81 are provided on the opposite sides of the outer peripheral surface 80*a* of the operation unit 80 in the aforementioned embodiment, the present disclosure is not limited to this. For example, one switch unit 83 and one enable switch 81 may alternatively be provided on one side of the outer peripheral surface 80*a* of the operation unit 80.

While the cross-section of the operation unit 80 has a substantially rectangular shape (the operation unit 80 has a substantially prismatic shape) in the aforementioned embodiment, the present disclosure is not limited to this. For example, the operation unit 80 may alternatively have a substantially cylindrical shape.

While the joystick 82 is provided on the end face 80*c* that intersects with the outer peripheral surface 80*a* of the operation unit 80 in the aforementioned embodiment, the present disclosure is not limited to this. In the present disclosure, it is only necessary to provide the joystick 82 at a position operable by the finger of the operator O while the operator O grasps the operation unit 80 to press the enable switches 81.

While the operation unit 80 is attached to the translation mechanism 70 in the aforementioned embodiment, the present disclosure is not limited to this. For example, the operation unit 80 may alternatively be attached to the arm portion 61.

While the joystick 82 is configured to operate the arm 60 in the mode for translating the tip end 4*d* of the medical device 4 in the predetermined plane (see FIG. 7) and the mode for rotating the medical device 4 about the tip end 4*d* of the medical device 4 (see FIG. 8) in the aforementioned embodiment, the present disclosure is not limited to this. For example, the joystick 82 may alternatively be configured to operate the arm 60 such that the medical device 4 translates along the longitudinal direction of the medical device 4.

While the moving speed of the tip end 4*d* of the medical device 4 changes according to the tilted state of the joystick 82, and the joystick 82 is configured to maximize the moving speed of the tip end 4*d* of the medical device 4 on the predetermined plane when the joystick 82 is maximally tilted in the aforementioned embodiment, the present disclosure is not limited to this. For example, the joystick 82 may alternatively be configured to maximize the moving speed of the tip end 4*d* of the medical device 4 on the predetermined plane only when the joystick 82 is maximally tilted.

While the switch units 83 are push-button switches in the aforementioned embodiment, the present disclosure is not limited to this. For example, the switch units 83 may alternatively be seesaw switches.

While after the tip end 4*d* of the medical device 4 moves the predetermined distance from the pivot position PP, the translation mechanism 70 is moved to translate the tip end 4*d* of the medical device 4 in the aforementioned embodiment, the present disclosure is not limited to this. For example, after the tip end 4*d* of the medical device 4 reaches the pivot position PP, the translation mechanism 70 may alternatively be moved to translate the tip end 4*d* of the medical device 4.

While the switch units 83 are provided on the opposite sides of the operation unit 80 in the aforementioned embodiment, the present disclosure is not limited to this. For example, the switch unit 83 may alternatively be provided on one side of the operation unit 80.

While the controller 31 performs both of setting the upper limit for the input signal from the joystick 82 and smoothing the input signal from the joystick 82 in the aforementioned embodiment, the present disclosure is not limited to this. For example, the controller 31 may alternatively perform only one of setting the upper limit for the input signal from the joystick 82 and smoothing the input signal from the joystick 82.

While the four arms 60 are provided in the aforementioned embodiment, the present disclosure is not limited to this. The number of arms 60 may alternatively be three.

While each of the arm portion 61 and the positioner 40 includes a 7-axis articulated robot in the aforementioned embodiment, the present disclosure is not limited to this. For example, each of the arm 60 and the positioner 40 may alternatively include an articulated robot having an axis configuration (six axes or eight axes, for example) other than the 7-axis articulated robot.

What is claimed is:

1. A surgical robot comprising:
   an arm configured to allow a medical device to be attached thereto; and
   an operation unit to which the medical device is attached, the operation unit physically supported by the arm at an end portion of the arm; wherein
   the operation unit includes a joystick and switch unit both of which are configured to operate movement of the medical device by the arm,
   the joystick is configured to operate the movement of the medical device by the arm such that a tip end of the medical device moves on a predetermined plane,
   the switch unit comprising a first switch and a second switch,
   the first switch configured to operate the movement of the medical device by the arm such that the tip end of the medical device moves along a longitudinal direction of insertion of the medical device into the patient,
   the second switch is configured to operate the movement of the medical device by the arm such that the tip end of the medical device moves along the longitudinal direction opposite to the direction of insertion of the medical device into the patient,
   the operation unit is movable along at least the longitudinal direction relative to the end portion of the arm,
   the joystick, and the switch unit are positioned on a surface of the operation unit,
   the joystick is configured to maximize a moving speed of the tip end of the medical device on the predetermined plane when the joystick is maximally tilted, and
   a time from when the switch unit is pressed until the moving speed of the tip end of the medical device along the longitudinal direction of the medical device is maximized is longer than a time from when the joystick is operated until the moving speed of the tip end of the medical device on the predetermined plane is maximized.

2. The surgical robot according to claim 1, wherein the switch unit includes a first switch configured to move the tip end of the medical device in a direction in which the medical device is inserted into a patient, along the longitudinal direction of the medical device, and a second switch configured to move the tip end of the medical device in a direction opposite to the direction in which the medical device is inserted into the patient.

3. The surgical robot according to claim 2, wherein
   the first switch is arranged on a side of the operation unit on which the medical device is inserted into the patient; and
   the second switch is arranged adjacent to the first switch on a side opposite to the side of the operation unit on which the medical device is inserted into the patient.

4. The surgical robot according to claim 1, wherein the switch unit is configured to increase a moving speed of the tip end of the medical device according to an increase in a length of time for which an operator presses the switch unit.

5. The surgical robot according to claim 1, wherein the surface of the operation unit comprises an outer peripheral surface, and the operation unit includes a pair of the switch units provided on each of opposite sides of the outer peripheral surface of the operation unit.

6. The surgical robot according to claim 5, wherein
   the operation unit further includes a pair of enable switches respectively configured to allow or disallow movement of the arm; and
   the pair of enable switches are provided on the opposite sides of the outer peripheral surface of the operation unit, respectively.

7. The surgical robot according to claim 1, wherein
   the arm includes an arm portion including an articulated robot, and a translation mechanism provided on a tip end side of the arm portion, the translation mechanism being configured to allow the medical device to be attached thereto, the translation mechanism being configured to translate the medical device in a direction in which the medical device is inserted into a patient; and
   until a pivot position that serves as a fulcrum for movement of the arm is set, the switch unit is operated such that the arm portion is moved to translate the tip end of the medical device.

8. The surgical robot according to claim 7, wherein
   after the pivot position is set, the switch unit is operated such that the arm portion is moved to translate the tip end of the medical device until the tip end of the medical device moves a predetermined distance from the pivot position; and
   after the tip end of the medical device moves the predetermined distance from the pivot position, the translation mechanism is moved to translate the tip end of the medical device.

9. The surgical robot according to claim 1, wherein the operation unit further includes a mode switch configured to switch between a mode in which the arm translates the medical device such that the tip end of the medical device moves on the predetermined plane and a mode in which the arm moves the medical device such that the medical device rotates about the tip end of the medical device.

10. The surgical robot according to claim 9, wherein on the operation unit, the mode switch is arranged in a vicinity of the joystick.

11. The surgical robot according to claim 1, wherein
    the arm includes an arm portion including an articulated robot, and a translation mechanism provided on a tip end side of the arm portion, the translation mechanism being configured to allow the medical device to be attached thereto, the translation mechanism being configured to translate the medical device in a direction in which the medical device is inserted into a patient; and
    the operation unit is attached to the translation mechanism.

12. The surgical robot according to claim 11, wherein the operation unit is attached to the translation mechanism so as to be adjacent to the medical device.

13. The surgical robot according to claim 1, wherein the joystick is configured to be operable by a finger of an operator while the operator grasps the operation unit.

14. The surgical robot according to claim 1, wherein
the switch unit increases the moving speed of the tip end of the medical device moves along the longitudinal direction of the medical device according to an increase in the length of time that the switch is pressed.

15. The surgical robot according to claim 1, wherein
the switch unit increases the moving speed at which the tip end of the medical device moves along the longitudinal direction of the medical device according to an increase in the length of time that the switch is pressed, such that the longer the switch is pressed the greater the speed of the tip end of the medical device along the longitudinal direction of the medical device.

16. A surgical robot comprising:
a robot arm including a plurality of joints, the robot arm being configured to allow a medical device to be attached to a tip end thereof; and
an operation unit to which the medical device is attached, the operation unit physically supported by the robot arm at the tip end; wherein
the operation unit includes a joystick configured to operate the robot arm to move the medical device,
the joystick is configured to be operable by a finger of an operator that grasps the operation unit,
the joystick is configured to operate the movement of the medical device by the arm such that a tip end of the medical device moves on a predetermined plane,
the operation unit further includes a switch unit configured to operate the movement of the medical device by the arm such that the tip end of the medical device moves along a longitudinal direction of the medical device,
the operation unit is movable along at least the longitudinal direction relative to the end portion of the arm,
the joystick, and the switch unit are positioned on a surface of the operation unit
the joystick is configured to maximize a moving speed of the tip end of the medical device on the predetermined plane when the joystick is maximally tilted, and
a time from when the switch unit is pressed until the moving speed of the tip end of the medical device along the longitudinal direction of the medical device is maximized is longer than a time from when the joystick is operated until the moving speed of the tip end of the medical device is maximized.

17. The surgical robot according to claim 16, wherein
the operation unit includes a mode switch; and
the mode switch is operated to switch between a mode in which the robot arm translates the medical device such that the tip end of the medical device moves on the predetermined plane and a mode in which the robot arm moves the medical device such that the medical device rotates about the tip end of the medical device.

18. A surgical robot comprising:
a robot arm including an arm portion including a plurality of joints, and a translation mechanism provided on a tip end of the arm portion, the translation mechanism being configured to allow a medical device to be attached thereto, the translation mechanism being configured to translate the medical device relative to the arm portion; and
an operation unit to which the medical device is attached, the operation unit physically supported by the translation mechanism of the robot arm; wherein
the operation unit includes:
a joystick configured to operate the arm portion to move the medical device; and
a switch unit configured to be operable by a finger of an operator, the switch unit being configured to operate the arm portion and/or the translation mechanism to translate the medical device,
the joystick and the switch unit are arranged apart from each other within a range operable by fingers of one hand of the operator in the operation unit,
the joystick is configured to operate the movement of the medical device by the arm such that a tip end of the medical device moves on a predetermined plane,
the switch unit is configured to operate the movement of the medical device by the arm such that the tip end of the medical device moves along a longitudinal direction of the medical device,
the operation unit is movable along at least the longitudinal direction relative to the end portion of the arm,
the joystick, and the switch unit are positioned on a surface of the operation unit,
the joystick is configured to maximize a moving speed of the tip end of the medical device on the predetermined plane when the joystick is maximally tilted, and
a time from when the switch unit is pressed until the moving speed of the tip end of the medical device along the longitudinal direction of the medical device is maximized is longer than a time from when the joystick is operated until the moving speed of the tip end of the medical device is maximized.

19. The surgical robot according to claim 18, wherein
the operation unit includes a mode switch; and
the mode switch is operated to switch between a mode in which the robot arm translates the medical device such that the tip end of the medical device moves on the predetermined plane and a mode in which the robot arm moves the medical device such that the medical device rotates about the tip end of the medical device.

20. The surgical robot according to claim 18, wherein
the surface of the operation unit comprises an outer peripheral surface,
the operation unit includes a pair of the switch units provided on opposite sides of the outer peripheral surface of the operation unit, and
at least one of the pair of switch units is configured to cause the arm portion and/or the translation mechanism to translate the medical device when the operator grasps the outer peripheral surface of the operation unit and operates the at least one of the pair of switch units.

21. A surgical robot comprising:
an arm configured to allow a medical device to be attached thereto; and
an operation unit comprising a joystick and a switch unit configured to operate movement of the medical device by the arm, wherein
a time from when the switch unit is pressed until the moving speed of a tip end of the medical device along a longitudinal direction of the medical device is maximized is longer than a time from when the joystick is operated until the moving speed of the tip end of the medical device on a predetermined plane is maximized.

22. A method of operating a surgical robot comprising an arm configured to allow a medical device to be attached thereto; and an operation unit comprising a joystick and a switch unit configured to operate movement of the medical device by the arm, the method comprising:
- pressing the switch unit to move a tip end of the medical device along a longitudinal direction of the medical device; and
- operating the joystick to move the tip end of the medical device on a predetermined plane, wherein
- a time from when the switch unit is pressed until the moving speed of the tip end of the medical device is maximized is longer than a time from when the joystick is operated until the moving speed of the tip end of the medical device is maximized.

* * * * *